United States Patent [19]

Ichihashi et al.

[11] Patent Number: 4,854,693

[45] Date of Patent: Aug. 8, 1989

[54] OPHTHALMIC DISEASE DETECTION APPARATUS

[75] Inventors: Tadashi Ichihashi, Toyohashi; Koichiro Kakizawa, Okazaki; Masunori Kawamura, Aichi, all of Japan

[73] Assignee: Kowa Company Ltd., Japan

[21] Appl. No.: 253,346

[22] Filed: Sep. 29, 1988

Related U.S. Application Data

[63] Continuation of Ser. No. 866,579, May 22, 1986, abandoned.

[30] Foreign Application Priority Data

May 22, 1985 [JP] Japan .................. 60-108298

[51] Int. Cl.$^4$ .............................................. A61B 3/10
[52] U.S. Cl. .................................. 351/221; 351/214
[58] Field of Search ................. 351/205, 214, 221; 128/303.1

[56] References Cited

U.S. PATENT DOCUMENTS

| | | | |
|---|---|---|---|
| 4,582,405 | 4/1986 | Müller et al. | 351/221 |
| 4,711,542 | 12/1987 | Ichihashi et al. | 351/221 |
| 4,743,107 | 5/1988 | Aizu et al. | 351/221 |

Primary Examiner—Rodney B. Bovernick
Assistant Examiner—P. M. Dzierzynski
Attorney, Agent, or Firm—Bruce L. Adams; Van C. Wilks

[57] ABSTRACT

An apparatus operates in an observation mode for determining a specific spot within the eye of a patient and operates in a measurement mode for measuring protein particles contained within the specific spot. The eye is illuminated with a slit light to determine a specific spot. A laser light is irradiated onto the determined specific spot. A scattered light scattered by protein particles is detected by a detector to measure the protein particles. Shutter members are actuated in the observation mode to unblock the slit light to thereby effect the determination of the specific spot, to block the laser light to thereby protect the eye, and to block the scattered light to thereby protect the detector, and actuated in the measurement mode to block the slit light to thereby prevent the slit light from being scattered by the protein particles, to unblock the laser light to thereby allow the laser light to be scattered by the protein particles and to unblock the thus scattered light to thereby effect the measurement of the protein particles.

6 Claims, 4 Drawing Sheets

OPHTHALMIC DISEASE DETECTION APPARATUS

This is a continuation of application Ser. No. 866,579, filed May 22, 1986, now abandoned.

BACKGROUND OF THE INVENTION

1. Field of the Invention

This is a continuation of Application Ser. No. 866,579, filed May 22, 1986 now abandoned.

This invention relates to an apparatus for detecting ophthalmic diseases in the lens of a patient's eye, and more particularly to an apparatus for detecting ophthalmic diseases by irradiating a laser beam via an optical system at one spot in the interior of a patient's eye, and by detecting the laser light back-scattered therefrom.

2. Description of the Prior Art

Cataracts are a common ophthalmic disease in which protein particles normally found in human crystalline lenses increase in size, thereby causing turbidity in the lens. Measuring the size and diameter of these protein particles is essential to effecting early detection of a cataract condition and to preparing preventative medical treatment thereof.

A human eye comprises transparent elements such as a cornea, crystalline lens, etc. Fine protein particles are contained in these transparent elements and exhibit Brownian movement. In normal disease-free eyes, the protein particles are distributed in the form of small diameter particles, however, in turbid eyes, the particles are of a larger diameter.

There is known in the art an apparatus for measuring the diameter of protein particles in the human eye, which comprises a laser for generating and then imaging a laser beam on a selected portion of the crystalline lens of the eye of a patient to be measured. Protein particles exhibiting Brownian movement travels through the portion of the lens of the eye on which the laser beam is focussed to cause the backscattering of the laser beam. Part of the laser light back-scattered in this manner is directed toward the eyepiece of a binocular microscope for monitoring, and another part thereof is directed toward a photomultiplier which converts the intensity of the back-scattered light into an electrical signal. This signal is input to an autocorrelator which determines an autocorrelation function with resepct to the fluctuation of the intensity of the back-scattered beam over time. The thus obtained correlation value is then used to calculate the relaxation time of the fluctuation of the intensity of the back-scattered beam. Accordingly, a diffusion coefficient can be further derived based thereon which may then be used to determine the diameter of the protein particles.

According to a prior art ophthalmic disease detection apparatus of this type, previously the control of luminous energy emitted from the laser light source and from a slit light source, and the manipulating of the OFF/ON of the shutter of a photomultiplier used to measure the intensity of the scattered light have been performed mechanically by hand, hence there has been a problem relating to the amount of time required in measuring.

SUMMARY OF THE INVENTION

It is therefore an object of the present invention to provide an apparatus for detecting ophthalmic diseases, which is capable of measuring the distribution of the protein particles in the eye.

It is another object of the present invention to provide an apparatus for detecting ophthalmic diseases, which is capable of effecting an easy and precise detection thereof.

In accordance with the present invention, the ophthalmic disease detecting apparatus disclosed herein includes means for focussing a laser beam and slit light at a selected spot in the lens of a patient's eye. The light back-scattered therefrom is photolectrically detected and coverted into an electrical signal which is analysed and evaluated for evidence of the existance of ophthalmic diseases. A further means is provided for optically controlling the quantity of the laser beam and the slit light, as well as the reception of back-scattered light so as to make available, during observation and measuring the automatic control of the luminosity and light emission of the respective light sources and the operation of the light receiving portion, and further to enable easy and reliable observation and measurement.

BRIEF DESCRIPTION OF THE DRAWINGS

The objects and features of the present invention will become more apparent from a consideration of the following detailed description taken in conjunction with the accompanying drawings in which.

DETAILED DESCRIPTION OF THE PREFERRED EMBODIMENTS

Figure 1:
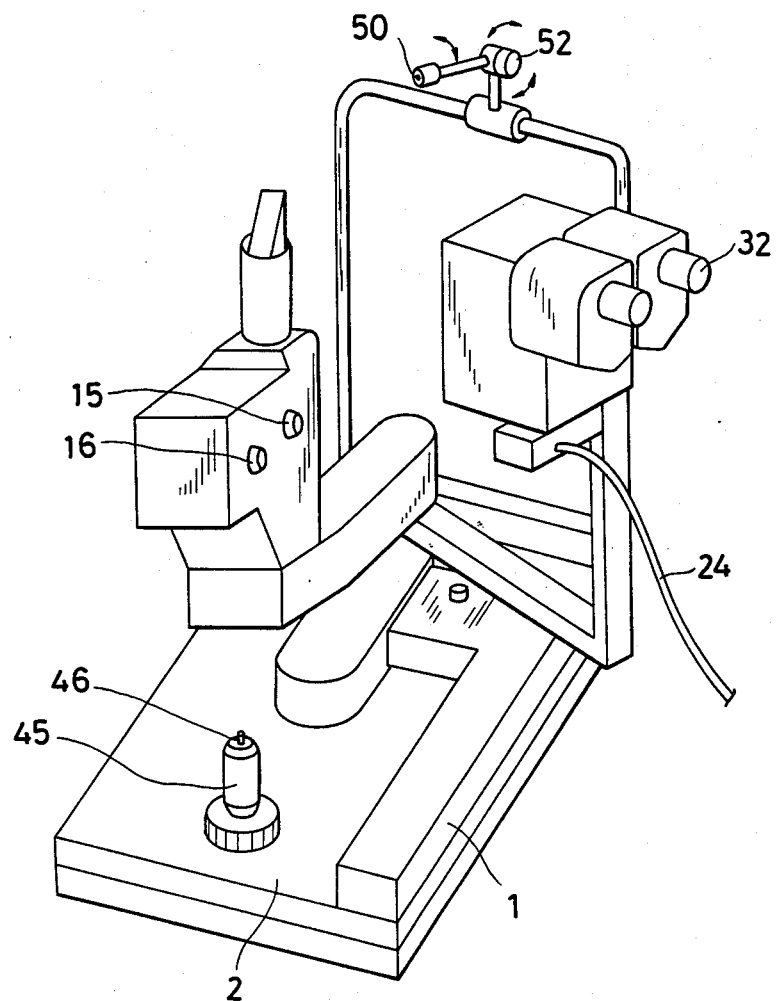
FIG. 1 is a schematic perspective view showing the overall structure of the apparatus of the present invention.
Figure 2:
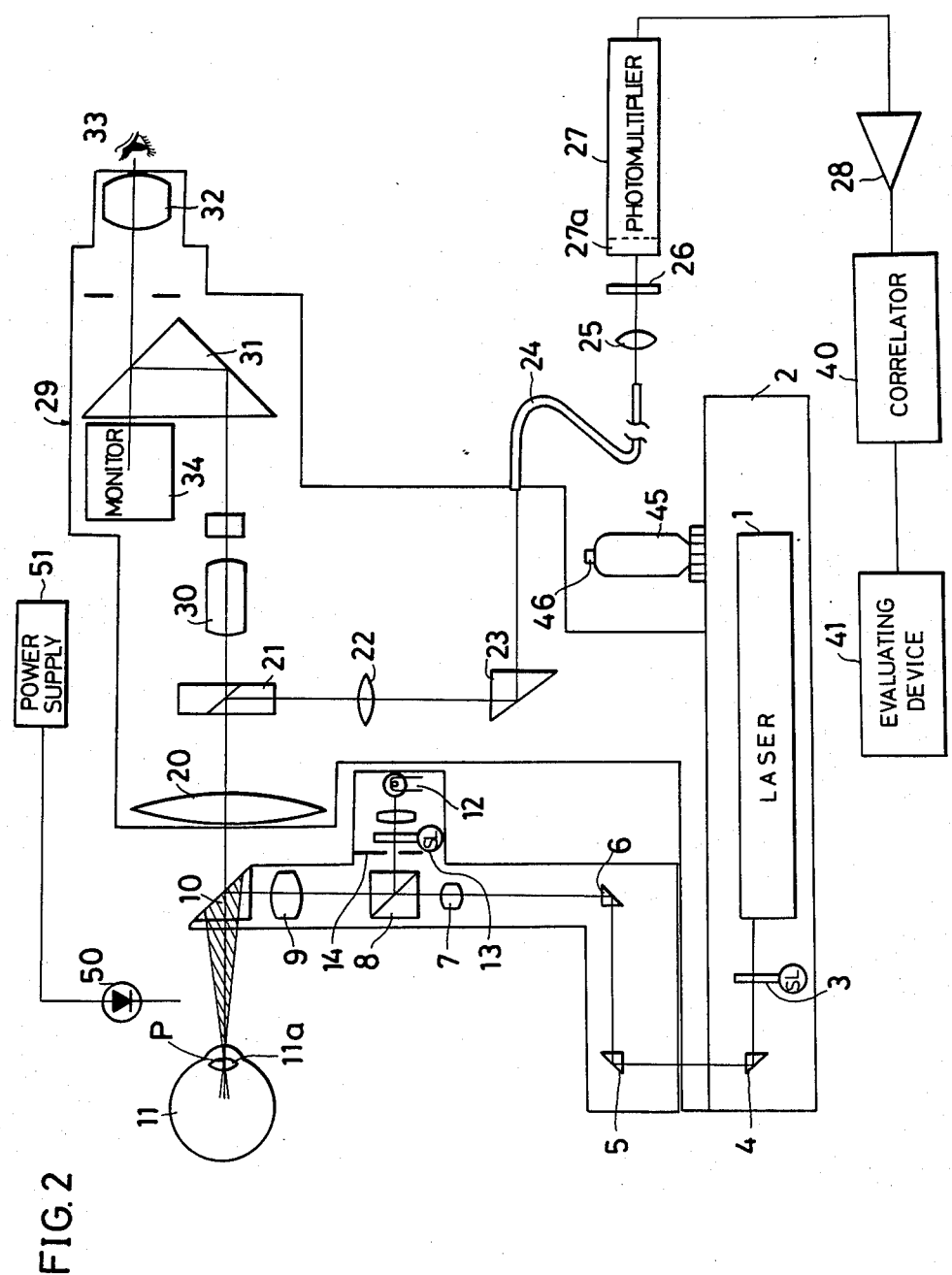
FIG. 2 is a block diagram showing the optical configuration of the apparatus.

FIG. 1 and FIG. 2 are simplified illustrations showing the configuration of an ophthalmic disease detecting apparatus according to the present invention. In the drawings, reference numeral 1 indicates a helium-neon or argon type laser light source which is provided on a base 2. The laser light emitted or irradiated form the laser light source 1 is passed through a laser filter 3, prisms 4, 5, and 6, a lens 7, a beam splitter 8, a lens 9, and a prism 10, and imaged in such a manner as to converge on spot of a crystalline lens 11a of a patient's eye 11.

A slit light source 12 is provided with the laser emitting portion of the apparatus, and the light emitted from this light source 12 passes through a slit light shutter 13 and a list 14 to form a slit light, and via the beam splitter 8, the lens 9, and the prism 10, and is imaged as a slit image on the crystalline lens 11a. Because the laser light emitted from the above mentioned laser light source 1 is as a spot of light, the slit light image is intended to illuminate the periphery of the laser light spot.

Adjustment as well as switching of the length of the slit along the lengthwise dimension of the list 14 can be carried out according to the manipulation of an adjust knob 15 and a switch knob 16, respectively.

Part of the laser light back-scattered from the measurement point in the crystalline lens 11a passes through the objective lens 20 of the detector 29, and is divided by a beam splitter 21, whereupon a portion of the divided light passes through a lens 22, a prism 23, an optical fiber 24, a lens 25, and a shutter 26, and then strikes a photomultipler 27 which performs the function of photoelectric converter. Another portion of the back-scattered light divided by the beam splitter 21 is directed in another direction and passes through a zoom lens 30 and a prism 31, whereupon it is enlarged and imaged on a monitoring plate 34. This image can be observed by an examiner 33 through an eyepiece 32.

The output of the photomultipier 27 is passed through an amplifier 28 and input to a correlator 40 which determines the correlation relating to the fluctuation of the intensity of back-scattered light detected by the photoelectric converter over time. The output of the correlator 40 is input to an evaluating device 41 where the distribution of protein particle diameters is investigated.

In the present invention, an eye attention lamp 50 comprising a light emitting diode fed by a power supply 51 is disposed in such a position as to enable the patient to fix the gaze of his eye thereto. The shade of light emitted by the eye attention lamp 50 is selected so as to differ from the shade of light emitted from the laser source 1. As an example, if the light emitted by the laser light source is red, the light emitted by the eye attention lamp may be green. The eye attention lamp 50 can be swivelled in the directions indicated by the arrows as shown in FIG. 1 according to a linkage 52, and hence is adjustable to the optimal position for any given patient.

An input device such as, for example, a joy stick 45 equipped with a push-button 46 is provided on the base 2, the manipulation of which effectuates the insertion of the laser filter 3, the slit light shutter 13, and the shutter 26 into the optical system, as well as the extraction of same therefrom.

Figure 3:
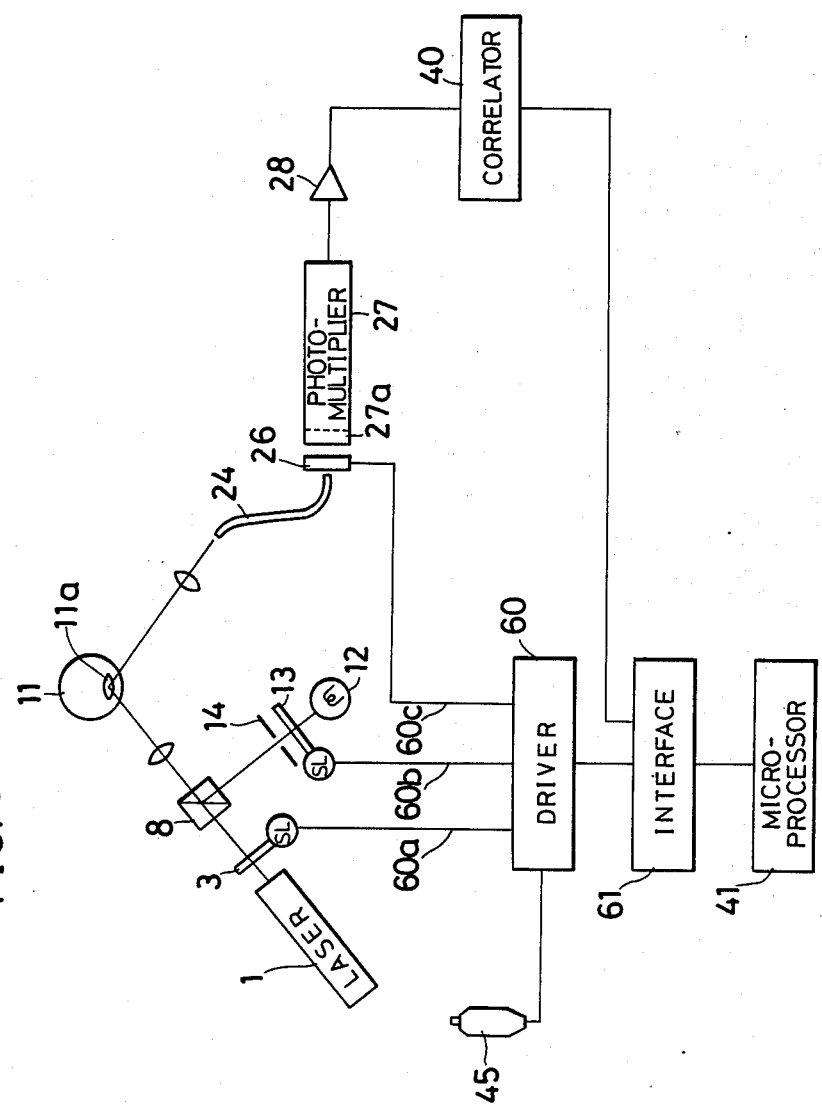
FIG. 3 is a block diagram showing the relationship between shutters and the driving system which drives the shutters.

As shown in FIG. 3, the joy stick 45 is connected to a driving circuit 60. This driving circuit 60 is connected via an interface circuit 61 to a microprocessor 41. The evaluating device shown in FIG. 2 can, for example, be realized by the microprocessor of FIG. 3. The laser filter 3, the slit light shutter 13, and the shutter 26 are connected to the driving circuit 60 via mutually adjacent lead wires 60a to 60c, respectively.

Figure 4:
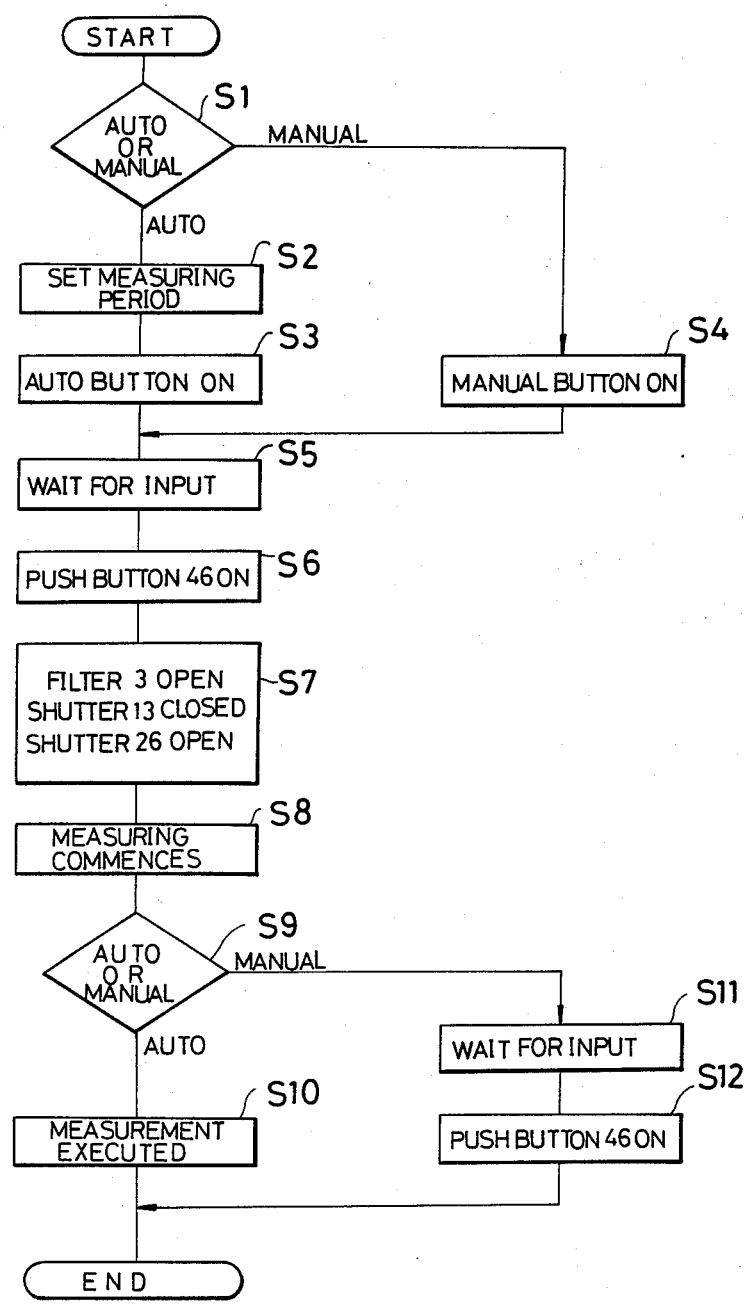
FIG. 4 is a flow chart showing the flow of the control process.

The operation of an apparatus with such an arrangement will be described in connection with the flow chart shown in FIG. 4. In step S1, a judgement is made as to whether the apparatus is in an auto-run (automatic) mode or in a manual run (hand operated) mode. When in auto-run, a measuring period is set at step S2, and in step S3, an auto-run button is put into ON. When in manual run, a manual run button is put into ON at step S4. Next, at step S5, an input for the joy stick is awaited. The observation mode precedes the measurement mode, and according to the observation mode the laser filter 3 is inserted into the optical path to block the laser light, the output of the laser light is reduced by, for example 1/10 mitigating the pain to the patient resulting from excessive brightness, the slit light shutter 13 is extracted from the optical path to unblock the slit light, the slit image of the slit 14 is formed on the crystalline lens 11a and covers an area inclusive of a specific measurement spot P, making the verification or determination of the measurement location easy, and then the shutter 26 is inserted into the optical path to block the incidence of the scattered light to the photomultiplier 27 at times other than during measuring.

In the next step S6, the push-button switch 46 of the joy stick 45 is actuated, and then at step S7 the laser filter 3 is extracted from the optical path to unblock the laser light, the laser output is returned to the normal state, the slit light shutter 13 is inserted into the light path so that the slit light is blocked and prevented from entering the detector, the shutter 26 is extracted from the optical path to unblock the scattered light, measuring preparations are carried out, and then at step S8, measuring commences.

During measuring, the light emitted from the laser source 1 passes through the optical system and is made to converge the measuring spot P.

Part of the light back-scattered from the measuring spot P is directed by the beam splitter 21 in the direction of the examiner 33 for observation, and simultaneously another portion thereof is sent by the beam splitter 21 to the photomultiplier 27 via the optical system comprising the lens 22, the prism 23, and the optical fiber 24. The photomultiplier 27 detects the intensity of the back-scattered light scattered by the protein particles within the measuring spot P in the crystalline lens 11a, subsequent to which the correlator 40 determines the correlation function relating to how the intensity of the light fluctuates over time. In response to the output of the correlator 4, the evaluating device 41 determines the distribution of protein particle diameters.

In the event a judgement is made at step S9 that the measurement will be performed automatically, the above mentioned measurement will be carried out at step S10 for exactly the period of time set at step S2. In the event a judgement is made that the measurement will be performed manually, the measurement may be carried out at steps S11 and S12 according to the manipulation of the joy stick 45.

While the invention has been described with reference to a preferred embodiment, it will be understood by those skilled in the art that various changes my be made and equivalents may be substituted for elements thereof without departing from the scope of the invention. In addition, many modifications may be made to adapt a particular situation or material to the teachings of the invention without departing from the essential scope thereof. Therefore, it is intended that the invention should not be limited to the particular embodiment disclosed as the best mode contemplated for carrying out the invention, but that the invention will include all embodiments falling within the scope of the appended claims.

We claim:

1. An apparatus for detecting ophthalmic diseases in the lens of a patient's eye comprising:
   a laser for producing a laser beam;
   means for focussing said laser beam at a selected spot in the lens of the patient's eye;
   a light source for illuminating a slit in order to produce a slit light image effective to determine the selected spot;
   photoelectric converting means for receiving light scattered by protein particles contained within the lens and converting said scattered light into an electrical signal;
   means for evaluating the electrical signal from said photoelectric converting means in order to measure the protein particles indicative of the existence of ophthalmic diseases;
   an optical filter movable for insertion into or extraction from an optical path for decreasing or increasing the quantity of the laser beam emitted from said laser;
   a first shutter movable for insertion into or extraction from an optical path for blocking or unblocking slit light from said light source which illuminates the slit;

a second shutter movable for insertion into or extraction from an optical path for blocking or unblocking the scattered light received by said photoelectric converting means; and means for selectively and simultaneously operating said filter and said first and second shutters so that, during an observation mode in which the selected spot is determined, said filter is inserted into the optical path to decrease the quantity of said laser beam, said first shutter is extracted from the optical path to unblock said slit light, and said second shutter is inserted into the optical path to block the scattered light impinging on said photoelectric converting means, and so that, during a measuring mode in which the protein particles are measured, said filter is extracted from the optical path to increase the quantity of said laser beam, said first shutter is inserted into the optical path to block said slit light, and said second shutter is extracted from the optical path to permit the scattered light to impinge on said photoelectric converting means.

2. An apparatus according to claim 1; wherein said operating means includes a joy stick.

3. In an apparatus operative in an observation mode of determining a specific spot within the eye of a patient and operative in a measurement mode for measuring protein particles contained within the specific spot of the eye: illuminating means for illuminating the eye with a slit light along a first optical path to determine a specific spot on the eye; irradiating means for irradiating a laser light along a second optical path onto the determined specific spot of the eye; detecting means of detecting scattered light scattered along a third optical path by protein particles contained within the specific spot of the eye to measure the protein particles; and control means comprising a first shutter insertable into and withdrawable from the first optical path for respectively blocking and unblocking slit light from the illuminating means, an optical filter insertable into and withdrawable from the second optical path for respectively filtering and not filtering the laser light from the irradiating means, and a second shutter insertable into and withdrawable from the third optical path for respectively blocking and unblocking the scattered light to be received by the detecting means, the control means being operative when the apparatus is in the observation mode to effect withdrawal of the first shutter for the first optical path and insertion of the second shutter into the third optical path when the filter is inserted into the second optical path, and being operative when the apparatus is in the measurement mode to effect insertion of the first shutter into the first optical path and withdrawal of the second shutter from the third optical path when the filter is withdrawn from the second optical path.

4. An apparatus according to claim 3; wherein the control means includes driving means for selectively driving the filter and shutters.

5. An apparatus according to claim 3; wherein the detecting means includes a photomultiplier for detecting intensity fluctuations of the scattered light due to Brownian movement of the protein particles.

6. An apparatus according to claim 5; wherein the detecting means includes an evaluating device for measuring the size of the protein particles according to the scattered light intensity fluctuation.

* * * * *